(12) United States Patent
Heinrichs (10) Patent No.: US 9,949,680 B2
(45) Date of Patent: Apr. 24, 2018

(54) DRAWWORKS

(71) Applicant: MHWIRTH GMBH, Erkelenz (DE)

(72) Inventor: Albrecht Heinrichs, Erkelenz (DE)

(73) Assignee: MHWIRTH GMBH, Erkelenz (DE)

( * ) Notice: Subject to any disclaimer, the term of this patent is extended or adjusted under 35 U.S.C. 154(b) by 676 days.

(21) Appl. No.: 14/384,389

(22) PCT Filed: Feb. 14, 2013

(86) PCT No.: PCT/EP2013/052956
§ 371 (c)(1),
(2) Date: Sep. 11, 2014

(87) PCT Pub. No.: WO2013/135452
PCT Pub. Date: Sep. 19, 2013

(65) Prior Publication Data
US 2015/0097149 A1 Apr. 9, 2015

(30) Foreign Application Priority Data

Mar. 12, 2012 (DE) .................... 10 2012 102 046

(51) Int. Cl.
*E21B 19/00* (2006.01)
*A61B 5/157* (2006.01)
(Continued)

(52) U.S. Cl.
CPC ............ *A61B 5/157* (2013.01); *A61B 5/1411* (2013.01); *A61B 5/1451* (2013.01); *A61B 5/1455* (2013.01); *A61B 5/1468* (2013.01); *A61B 5/14532* (2013.01); *A61B 5/150022* (2013.01); *A61B 5/15151* (2013.01); *A61B 5/15161* (2013.01); *A61B 5/15176* (2013.01); *A61B 5/150297* (2013.01); *A61B 5/150358* (2013.01); *A61B 5/150419* (2013.01);
(Continued)

(58) Field of Classification Search
CPC ........... E21B 19/008; B66D 1/14; B66D 1/28; B66D 1/82
See application file for complete search history.

(56) References Cited

U.S. PATENT DOCUMENTS 4,458,882 A * 7/1984 Schorling ................ B66D 1/28
254/332
2005/0133773 A1 6/2005 Heinrichs et al.
2008/0277637 A1 11/2008 Heinrichs

FOREIGN PATENT DOCUMENTS

CN 2651225 Y 10/2004
CN 201176376 Y 1/2009
(Continued)

OTHER PUBLICATIONS

English translation of FR 2,537,964.*

*Primary Examiner* — Sang K Kim
*Assistant Examiner* — Nathaniel L Adams
(74) *Attorney, Agent, or Firm* — Norman B. Thot (57) ABSTRACT

A drawworks for a drilling device for lowering and hoisting a load such as a drill string or parts thereof includes a frame comprising a first bearing point, a second bearing point, and a third bearing point, a winding drum, and a first bearing device connected to the frame for the winding drum. The first bearing device is arranged so that a center of respective bearing forces is located at each of the first bearing point, at the second bearing point, and at the third bearing point.

7 Claims, 5 Drawing Sheets

(51) Int. Cl.
*A61B 5/15* (2006.01)
*G01N 33/487* (2006.01)
*A61B 5/145* (2006.01)
*A61B 5/1455* (2006.01)
*A61B 5/1468* (2006.01)
*A61B 5/151* (2006.01)
*A61B 10/00* (2006.01)

(52) U.S. Cl.
CPC ...... *A61B 5/150503* (2013.01); *A61B 10/007* (2013.01); *A61B 10/0045* (2013.01); *G01N 33/4875* (2013.01); *A61B 5/15107* (2013.01); *A61B 5/15115* (2013.01)

(56) References Cited

FOREIGN PATENT DOCUMENTS

| | | |
|---|---|---|
| CN | 102336374 A | 2/2012 |
| DE | 536 115 C | 11/1931 |
| DE | 38 19 447 C2 | 5/1990 |
| FR | 2 537 964 A1 | 6/1984 |
| WO | WO 03/072904 A1 | 9/2003 |
| WO | WO 2005/035427 A1 | 4/2005 |

\* cited by examiner

DRAWWORKS

CROSS REFERENCE TO PRIOR APPLICATIONS

This application is a U.S. National Phase application under 35 U.S.C. § 371 of International Application No. PCT/EP2013/052956, filed on Feb. 14, 2013 and which claims benefit to German Patent Application No. 10 2012 102 046.9, filed on Mar. 12, 2012. The International Application was published in German on Sep. 19, 2013 as WO 2013/135452 A1 under PCT Article 21(2).

FIELD

The present invention relates to a drawworks for a drilling device for lowering and hoisting a load, in particular a drill string or parts thereof, having a frame, a winding drum, and a bearing device connected to the frame for the winding drum.

BACKGROUND

The load in such drawworks is routinely fastened to a flexible traction element which is usually formed as a steel cable. For the purpose of lowering and hoisting, the winding drum is rotatably driven so that the flexible traction means is unwound or wound up.

In the case of drawworks according to the prior art, as are described, for example, in WO 03/072904 A1, the winding drum is fastened in a rotationally fixed manner to a winding shaft whose axis extends approximately parallel to the longitudinal sides of the frame. The winding shaft is mounted in bearing blocks which are fixedly connected to the frame beyond the two end sides of the winding drum. As seen from the winding drum, a braking device acting on the winding shaft is provided beyond one bearing block. It is routinely designed as a disk brake device and comprises a brake disk, which is connected to the winding shaft in a rotationally fixed manner, and brake caliper arrangements fastened to the frame. The brake disk can also be arranged directly on the flanged drum disk.

As seen from the winding drum, there is provided, beyond the other bearing block, a gear unit which, in the case of the exemplary embodiment described in WO 03/072904 A1, comprises two individual gearboxes and a summing gear connected to the winding shaft. The gearboxes are fixedly connected to the frame. The housing of the summing gear is connected to the frame via a torque support.

In order to avoid a situation in which distortions of the frame (which are unavoidable if, for example, the underlying surface on which the frame is mounted subsides, or which can occur during temperature changes) result in stresses in the winding shaft and the gear arrangement which increase wear or even damage the entire drawworks, the gearboxes are connected to the summing gear via flexible couplings.

In another drawworks, the summing gear is likewise fixedly connected to the frame. A flexible coupling is then provided between the output shaft of the summing gear and the winding shaft.

Although, on account of the flexible couplings, certain distortions of the frame can be compensated for, care must be taken in the case of these drawworks to ensure that the frame is precisely oriented on the underlying surface to provide an alignment or parallel-running of all the axes and shafts of the drawworks since the couplings permit only limited deviations from the parallel or aligned orientations of the axes or shafts and the loading of the couplings increases as the deviations increase. The frame must therefore be designed to be as distortion-resistant as possible, which unadvantageously increases both its weight and its manufacturing costs. Experience has moreover shown that the frame must be routinely realigned in the course of the operation of a drawworks since the underlying surface subsides on account of the dynamic load changes which act on the drawworks during the lifting and lowering of loads.

SUMMARY

An aspect of the present invention is to provide a drawworks which is improved with respect to the aforementioned problem.

In an embodiment, the present invention provides a drawworks for a drilling device for lowering and hoisting a load such as a drill string or parts thereof which includes a frame comprising a first bearing point, a second bearing point, and a third bearing point, a winding drum, and a first bearing device connected to the frame for the winding drum. The first bearing device is arranged so that a center of respective bearing forces is located at each of the first bearing point, at the second bearing point, and at the third bearing point. The "three-point bearing" provides that any distortions of the frame have only minor effects on the adjustment of the winding shaft.

BRIEF DESCRIPTION OF THE DRAWINGS

The present invention is described in greater detail below on the basis of embodiments and of the drawings in which.

DETAILED DESCRIPTION

In an embodiment of the present invention, precisely one of the three bearing points can, for example, be provided on that side of the winding drum on which a braking device for the winding drum is provided. If (as in most cases) the winding drum is fastened to a winding shaft in a rotationally fixed manner, the bearing point can be arranged and formed so that it accommodates the winding shaft in a suitable rotary bearing. A part of a braking device, for example, a brake disk of a disk brake device, can be provided in a region of the winding shaft which projects from the rotary bearing on the side pointing away from the winding drum. The bearing arrangement for the winding shaft can be designed so that the winding shaft is mounted fixedly in the axial direction of the winding shaft but pivotably about axes extending perpendicular to the winding shaft. As a result of the bearing which is fixed in the axial direction, it is provided that a gap allowing a brake disk movement in the axial direction need not be present between the brake shoes and the brake disk, which gap would unadvantageously extend the actuating travel of the brake shoes unless the brake calipers were likewise displaceable in a direction parallel to the longitudinal axis of the winding shaft, in other words, were mounted in a "floating" manner.

In order to achieve pivotability about axes extending perpendicular to the winding shaft, the first bearing arrangement may, for example, comprise a pendulum bearing, for example, a pendulum roller bearing.

The other two bearing points of the bearing device can, for example, be provided on the side of the winding drum on which a rotary drive device for the winding drum is arranged. These two bearing points can, for example, be arranged on mutually opposite sides of the longitudinal axis of the winding shaft, i.e., on both sides of the winding drum in a view perpendicular to the frame.

The two bearing points can be formed by a second bearing device in which the rotary drive-side region of the winding shaft is mounted. The bearing device can, for example, be designed so that a displacement of the winding shaft relative to the frame in the direction parallel to the winding shaft and pivoting movements about axes extending perpendicular to the winding shaft are possible. The second bearing device can, for example, be provided on a drive unit which comprises, in particular, a gear device transmitting rotary drive power to the winding shaft and at least one rotary motor operatively connected to the gear device. As a result of this measure, which is for the first time made possible by the "three-point bearing" according to the present invention, it is possible to dispense with flexible couplings allowing distortions of the frame to a certain extent. The rotary drive unit can be connected to the winding shaft directly, i.e., without the interposition of one or more flexible couplings. Any distortions of the frame or displacements in the direction of the longitudinal axis of the winding shaft nevertheless do not lead to stresses in the winding shaft since the rotary drive device is no longer displaced by distortions or thermal expansions of the frame relative to the winding shaft.

Each bearing point of the second bearing device can, for example, comprise second bearing arrangements allowing longitudinal displacements parallel to the axial direction of the winding shaft and pivoting movements about axes extending perpendicular to the winding shaft.

Each second bearing arrangement can have a pendulum bearing, for example, a pendulum sliding bearing.

In order to allow the displacement in a direction parallel to the longitudinal axis of the winding shaft, each second bearing arrangement can, for example, comprise a bearing bolt which is connected to the drive device and which is accommodated by the pendulum sliding bearing so that it can be displaced in the direction parallel to the axial direction of the winding shaft.

An exemplary embodiment of the drawworks according to the present invention is illustrated schematically in the drawings and is described below.

The exemplary embodiment of a drawworks according to the present invention, designated overall by 100 in the drawing, comprises a frame 1 on which the key components of the drawworks 100 are mounted. In order to hoist and lower and, depending on the use conditions, also to hold a load, in particular a drilling device, a drill string, or parts thereof, the drawworks 100 comprises a winding drum 2 which is fastened in a rotationally fixed manner to a winding shaft 3 and of which the center longitudinal axis S extends parallel to the longitudinal sides 4 of the frame 1.

Figure 5:
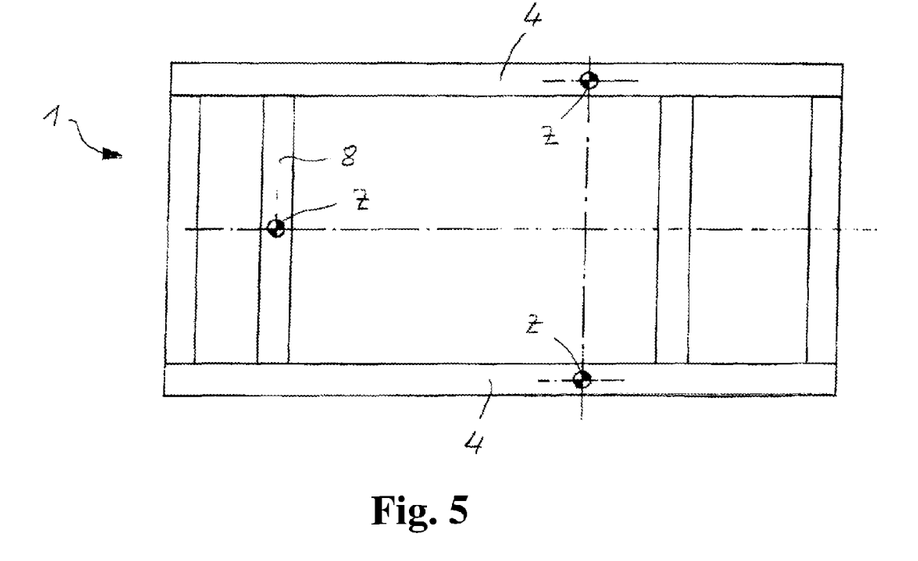
FIG. 5 shows the position of the bearing force centers of the "three-point bearing", embodied in the drawworks according to the present invention, on the frame.

To mount the winding shaft 3, the drawworks 100 comprises a bearing device which is designated overall by 5 and which is designed as a "three-point bearing" such that the centers Z (see FIG. 5) of the bearing forces are located at three bearing points $S_1$, $S_2$, $S_3$ of the frame 1.

Figure 4:
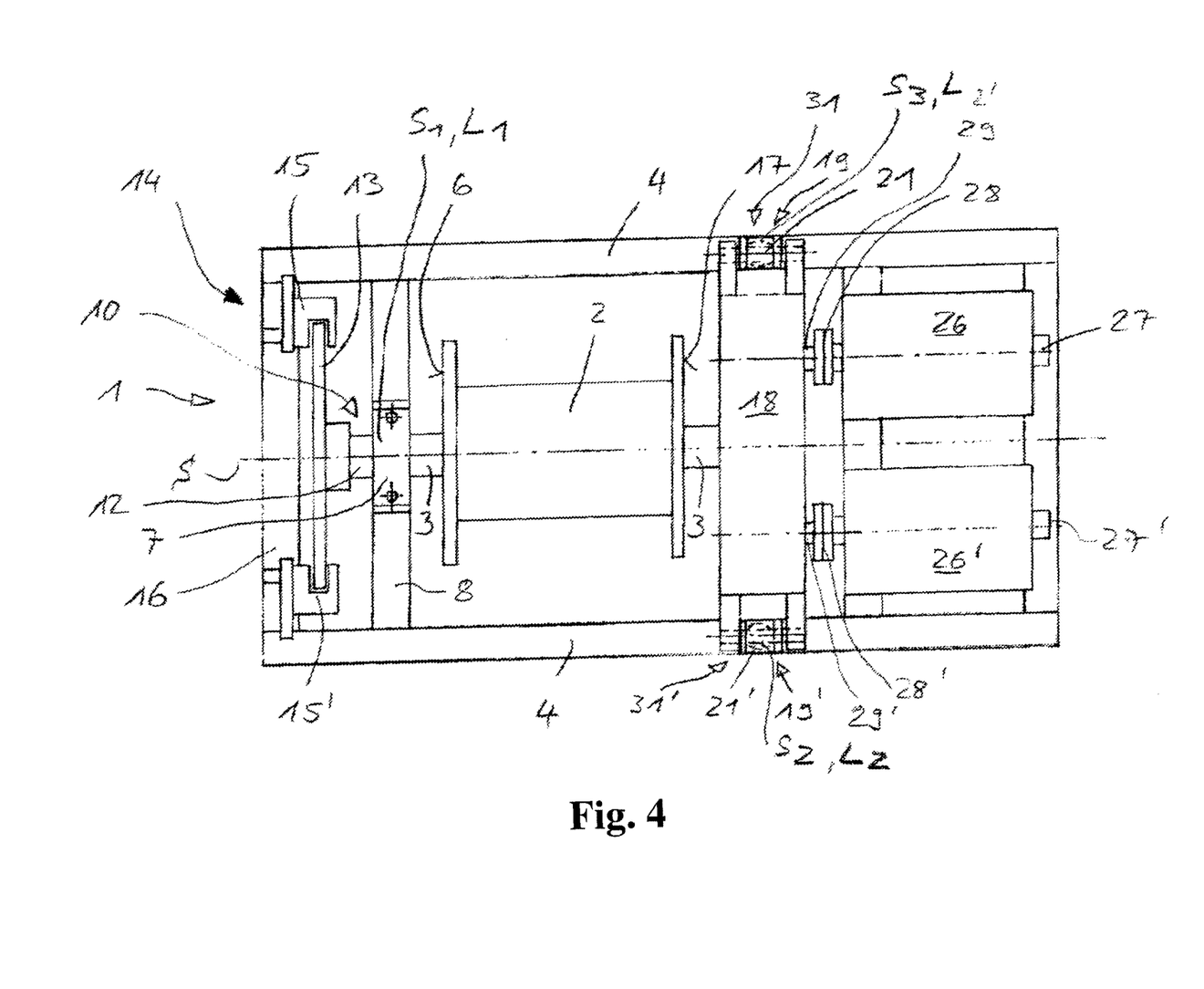
FIG. 4 shows a view as shown in FIG. 1 from above.
Figure 6:
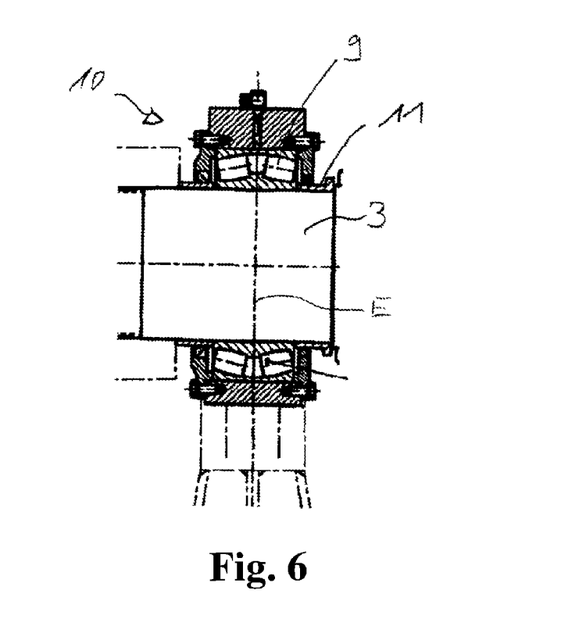
FIG. 6 shows the detail Y in FIG. 1 in an enlarged view.

For this purpose, in the exemplary embodiment illustrated in the drawing, the bearing device 5 has, to the left of the left end side 6 of the winding drum 2, a bearing block 7 which is fixedly connected to a crossmember 8 of the frame 1 (see in particular FIG. 4). The bearing block 7 comprises a first bearing arrangement 10 designed as a pendulum roller bearing 9. This arrangement comprises, as can be seen in FIG. 6, an inner bearing shell 11 which is fixedly connected to the winding shaft 3. The winding shaft 3 is thus fixed in the direction of the axis S by means of the pendulum roller bearing but is pivotable about axes perpendicular to the axis S which are located in the bearing plane E. The winding shaft 3 passes through the pendulum roller bearing 9. A disk brake 13 of a disk brake arrangement 14 is fastened at the region 12 pointing away from the winding drum 2. This arrangement moreover comprises two or more brake calipers 15, 15' which are fixedly connected to a further crossmember 16 of the frame 1.

Figure 7:
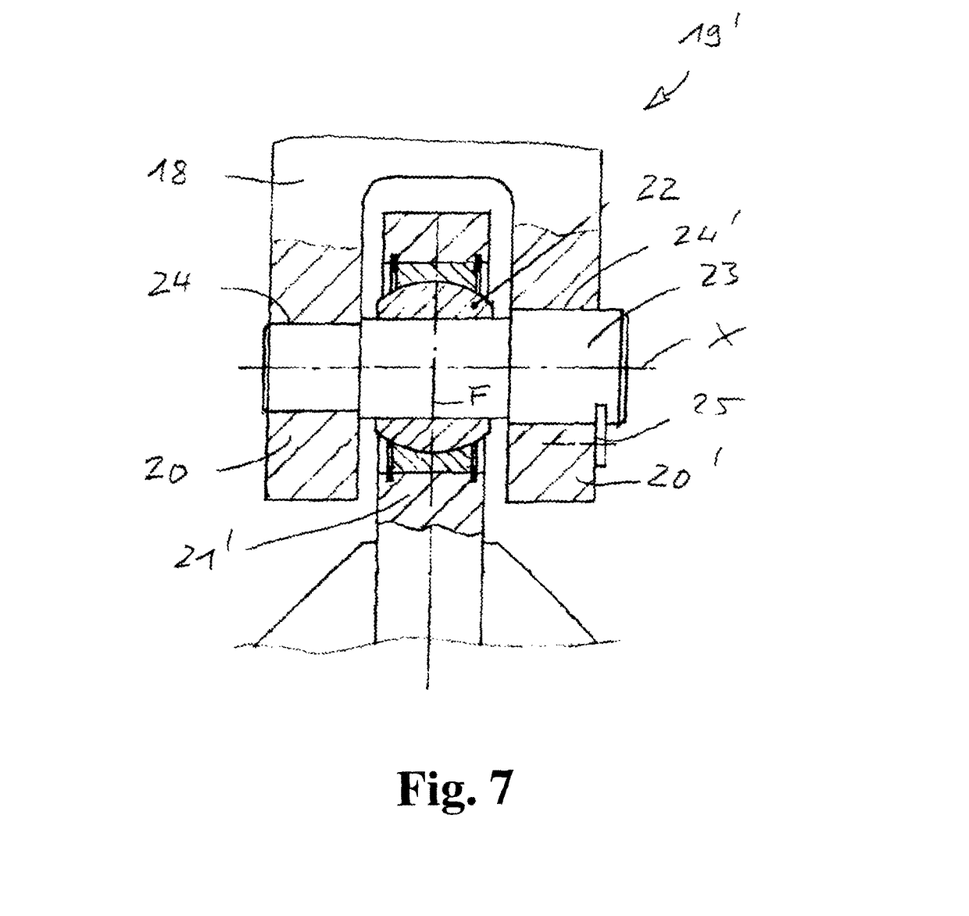
FIG. 7 shows the detail X in FIG. 1 in an enlarged view, partially sectioned.

Beyond the end side 17 of the winding drum 2 as illustrated on the right in FIG. 4, the winding shaft 3 is rotatably mounted in a bearing device 18 which forms a further part of the bearing device 5. As can be seen in particular in FIG. 4, the bearing device 18 comprises two fork-shaped receptacles 19, 19' arranged on both sides of the center longitudinal axis S of the winding shaft 3. Second bearing points $L_2$, $L_2$ are formed by the bearing device 18. As can be seen in FIG. 7, which shows the fork-shaped receptacle 19' in an enlarged detail view, a bearing block 21, 21' engages between the two prongs 20, 20' of the receptacle. Both bearing blocks 21, 21' are fixedly connected to a respective frame side 4. Each bearing block 21, 21' accommodates a pendulum bearing 22 designed as a sliding bearing. To connect the bearing device 18 to the bearing blocks 21, 21', in each case a stepped bolt 23 is provided which passes through the respective pendulum bearing 22 and which, in the exemplary embodiment illustrated in the drawing (see in particular FIG. 7), is inserted from the right into eyes 24, 24' provided for this purpose and through the pendulum bearing 22 and fixed in its longitudinal direction by means of a locking element 25. The stepped bolt 23 passes slidingly through the pendulum bearing with its central region. Since the clearance between the two prongs 20, 20' is greater than the width of the respective bearing block 21, 21', a displacement, corresponding to the size of the difference between clearance and width, can take place between the bearing device 18 and the bearing blocks 21, 21' in the direction of the stepped bolt axis X. Pivoting movements about axes located perpendicular to the stepped bolt axis X and in the bearing plane F can furthermore take place between the stepped bolt 23 and hence the bearing device 18. In this respect, in the drawworks 100 according to the present invention, a deformation of the frame 1 is possible to an extent which is limited by the design of the pendulum bearings 22 and of the pendulum roller bearing 9, which does not lead to stresses on the winding shaft 3.

In the exemplary embodiment of a drawworks 100 according to the present invention as illustrated in the drawing, the bearing device 18 is designed as a summing gear. The winding shaft 3 is the gear output shaft or is connected thereto in a rotationally fixed manner and is supported by it. A flexible coupling for connecting the gear output shaft and the winding shaft 3 is therefore not necessary. The expenditure associated with the production and the installation of the flexible coupling does not therefore need to be incurred in the drawworks according to the present invention. The overall length of the drawworks according to the present invention is furthermore advantageously shortened as a result of the omission of the flexible coupling.

Figure 1:
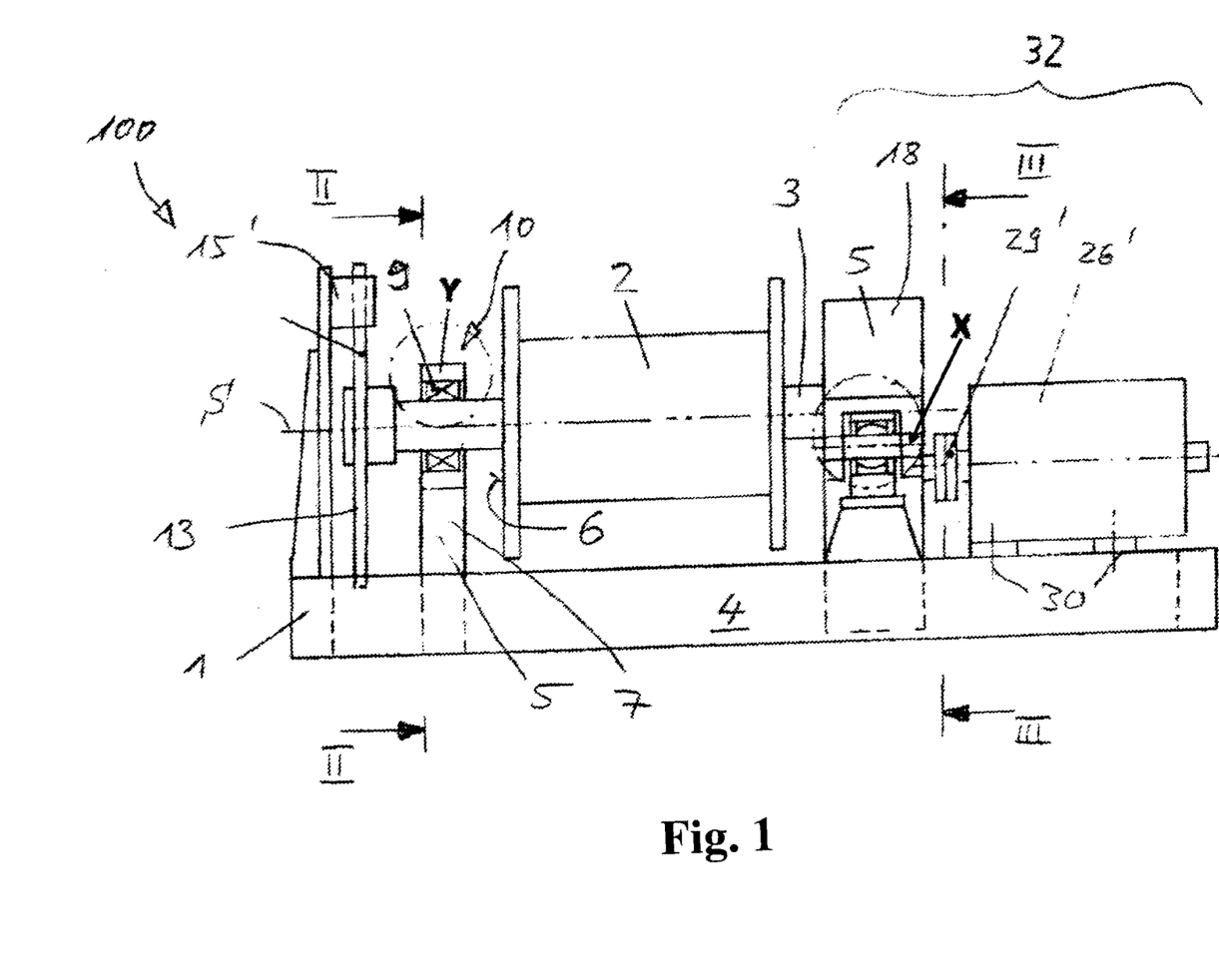
FIG. 1 shows a side view of this drawworks perpendicular to the center longitudinal axis of the winding shaft.
Figure 2:
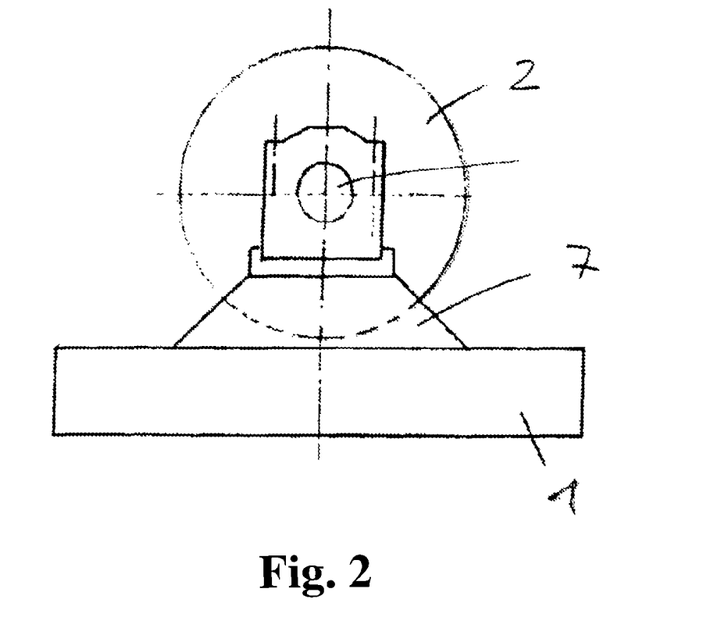
FIG. 2 shows the view II-II in FIG. 1.
Figure 3:
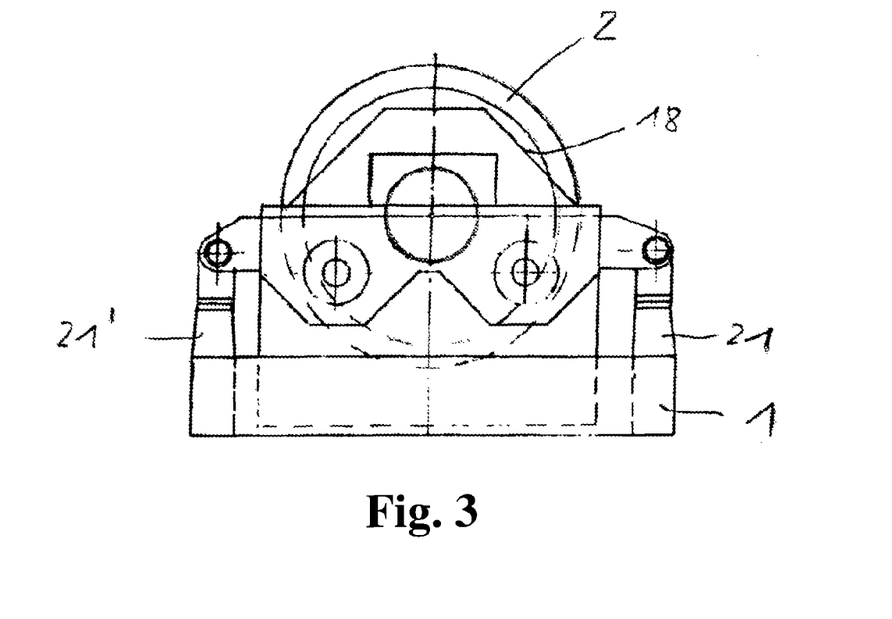
FIG. 3 shows the view III-III in FIG. 1.

In the exemplary embodiment of the drawworks according to the present invention as illustrated in the drawing, a rotary drive device 32 (see FIG. 1) with two rotary drive motors 26, 26' are provided on the side, opposite to the winding drum 2, of the bearing device 18 comprising the gear. These rotary drive motors 26, 26' can be designed in particular so that they can be driven electrically, pneumatically or hydraulically. In the exemplary embodiment shown, they are electric motors. In order to provide an electrical insulation between the drive shafts 27, 27' from the remainder of the drawworks 100, the drive shafts are connected via insulating couplings 28, 28' to the input shafts 29, 29' of the bearing device 18 designed as a summing gear. In particular, if, instead of electric motors, hydraulically or pneumatically operated rotary drive motors 26, 26' are used, the insulating couplings can be dispensed with. Since motors operated in this way routinely also have a smaller overall shape and a lower weight combined with a power which is comparable to electric motors, they can then also be mounted directly onto the bearing device 18. No further fastening 30 to the frame is then required, as is the case with the electric motors present in the exemplary embodiment illustrated.

For the sake of completeness, it should be mentioned that, instead of two drive motors, it is also possible for only one or else more than two to be provided. The drive motor or motors can also be arranged on a frame separate from the frame 1 and be connected via relatively long shafts to the bearing device 18 comprising the gear. The gear can be a single- or multistage gear and have a single-speed or multispeed design. The gear can be integrated into the bearing device 18 or else flanged onto the latter. It is also conceivable to fasten slow-running rotary drives to the bearing device 18 and connect them directly to the winding shaft 3.

The second bearing arrangements 31, 31' provided on the bearing device 18 also do not need to be arranged symmetrically to the center longitudinal axis S of the winding shaft 3, as in the exemplary embodiment illustrated in the drawing.

In summary, a drawworks according to the present invention has the following advantages:

Stresses in the winding shaft and in the gear are avoided due to the three-point bearing.

The frame no longer needs to be aligned as precisely as in drawworks belonging to the prior art, with the result that the construction and the installation of the drawworks according to the present invention is simplified.

The frame of the drawworks can be designed to be less stable and thus more lightweight.

The assembly and dismantling of a drawworks according to the present invention are simplified due to a smaller number of components.

The overall length of the drawworks according to the present invention can be shortened due to the omission of flexible couplings which are otherwise required in some cases.

LIST OF REFERENCE NUMERALS

100 Drawworks
1 Frame
2 Winding drum
3 Winding shaft
4 Frame side
5 Bearing device (gear unit)
6 Left end side
7 Bearing block
8 Crossmember
9 Pendulum roller bearing
10 First bearing arrangement
11 Inner bearing shell
12 Region
13 Disk brake
14 Disk brake arrangement
15, 15' Brake calipers
16 Crossmember
17 Right end side
18 Bearing device (gear unit)
19, 19' Receptacles
20, 20' Prongs
21, 21' Bearing blocks
22 Pendulum bearing
23 Stepped bolt
24, 24' Eyes
25 Locking element
26, 26' Rotary drive motors
27, 27' Drive shafts
28, 28' Couplings
29, 29' Input shafts
30 Fastening
31, 31' Second bearing arrangements
32 Rotary drive device
E Bearing plane
F Bearing plane
S Axis
$S_1$, $S_2$, $S_3$ Bearing points
X Stepped bolt axis
$L_1$ First bearing point
$L_2$, $L_{2'}$ Second bearing points
Z Centers The present invention is not limited to embodiments described herein; reference should be had to the appended claims.

What is claimed is:

1. A drawworks for a drilling device for lowering and hoisting a load, the drawworks comprising:
   a frame comprising a first bearing point, a second bearing point, a third bearing point, and a center longitudinal axis;
   a winding drum;
   a first bearing device connected to the frame for the winding drum,
   a braking device arranged on a first side of the drawworks, the braking device being configured to brake the winding drum; and
   a rotary drive device for the winding drum arranged on a second side of the drawworks,
   a second bearing device configured to have the rotary drive-side region of the winding shaft be mounted therein, the second bearing point and the third bearing point being formed by the second bearing device,
   wherein,
   the first bearing point is arranged on the first side of the drawworks on which the braking device is arranged;
   the second bearing point and the third bearing point are each arranged on the second side of the drawworks on which the rotary drive device is arranged,
   the first bearing point is arranged on the center longitudinal axis of the frame,
   each of the second bearing point and the third bearing point are arranged on mutually opposite sides of the center longitudinal axis of the frame, the second bearing device is configured to be displaceable relative to the frame and to allow a pivoting movement about axes extending perpendicular to the axis of the winding shaft, and the second bearing point and the third bearing point each comprise a second bearing arrangement, each second bearing arrangement being configured to allow a longitudinal displacement of the second bearing device parallel to an axial direction of the winding shaft and a pivoting movement about axes extending perpendicular to the axial direction of the winding shaft, each second bearing arrangement comprising a pendulum sliding bearing and a bolt which is configured to be connected to or inserted into the second bearing device and to be accommodated by the pendulum sliding bearing so that the pendulum sliding bearing is displaceable in a direction parallel to an axial direction of the winding shaft.

2. The drawworks as recited in claim 1, wherein the first bearing point comprises a first bearing arrangement in which a winding shaft is mounted so as to be fixed in an axial direction with respect to the frame and to pivot about axes which extend perpendicular to the axial direction with respect to the winding shaft, wherein the winding shaft is connected to the winding drum so as to be rotationally fixed.

3. The drawworks as recited in claim 2, wherein the first bearing arrangement comprises a pendulum bearing.

4. The drawworks as recited in claim 3, wherein the pendulum bearing is a pendulum roller bearing.

5. The drawworks as recited in claim 2, wherein the winding shaft comprises a rotary drive-side region.

6. The drawworks as recited in claim 1, wherein the second bearing device is arranged on a drive unit.

7. The drawworks as recited in claim 6, wherein the drive unit comprises a gear device configured to transmit a rotary drive power to the winding shaft.

* * * * *